(12) United States Patent
Lee et al.

(10) Patent No.: US 7,037,903 B2
(45) Date of Patent: May 2, 2006

(54) METHOD FOR USING THYMOSIN β-10 FOR GENE THERAPY OF SOLID MALIGNANT TUMORS

(76) Inventors: Je-Ho Lee, 10-19 Sussomisi 2000 Officetel, 725 Suso-dong, Kangnam-gu, Seoul, 135-888 (KR); Seung-Hoon Lee, 102-186, Yongdu 2-dong, Dongdaemoon-gu, Seoul, 102-186 (KR)

( * ) Notice: Subject to any disclaimer, the term of this patent is extended or adjusted under 35 U.S.C. 154(b) by 313 days.

(21) Appl. No.: 10/231,845

(22) Filed: Aug. 30, 2002

(65) Prior Publication Data

US 2003/0099617 A1     May 29, 2003

(30) Foreign Application Priority Data

Oct. 10, 2001     (KR) ............................... 2001-63524

(51) Int. Cl.
    *A61K 48/00*     (2006.01)
(52) U.S. Cl. ........................................ 514/44; 536/23.1
(58) Field of Classification Search ................ 514/44; 536/23.1
    See application file for complete search history.

(56) References Cited

U.S. PATENT DOCUMENTS

2002/0168771 A1* 11/2002 Gamerman ................. 435/456

OTHER PUBLICATIONS

Verma et al. (1997) Gene Therapy-promises, problems and prospects. Nature. 389,:239-242.*
Marshall (1995)Gene Therapy's Growing Pains. Science. 269:1050-1055.*
Orkin et al. (1995) Report and recommendations of the panel to assess the NIH investment in research on gene therapy, 1-44.*
Arnold et al., (2002) Chromosome 8 genetic analysis and phenotypic characterizaton of 21 ovarian cancer cell lines. Cancer Genetics and Cytogeneitcs139:109-114.*
Kammerer et al. (2003) Expression of Tumor Markers on Breast and Ovarian Cancer Cell Lines. Anticancer Research 23:1051-5.*
Jung et al. (2002) CT and MR Imaging of Ovarian Tumors with Emphasis on Differential Diagnosis. Radiographics, 22:1305-25.*

(Continued)

*Primary Examiner*—Deborah Crouch
*Assistant Examiner*—Louis D. Lieto
(74) *Attorney, Agent, or Firm*—Gates & Cooper LLP

(57) ABSTRACT

A method for using thymosin β-10 for cancer treatment by expressing thymosin β-10 in solid malignant tumor cells. More precisely, the present invention relates to a cancer treatment method wherein thymosin β-10 is expressed in solid malignant tumor cells by infecting adenovirus including thymosin β-10. The gene therapy for cancer using thymosin β-10 of the present invention is very effective for the treatment of ovarian cancer, cervical cancer, stomach cancer and lung cancer.

4 Claims, 7 Drawing Sheets

A.

B.

OTHER PUBLICATIONS

Huard (1995) The Route of administration is a major determinant of the transduction efficeiency of rat tissues by adenoviral recombinants. Gene Ther. 2:107-15.*

McCluskie et al. (1999) Route and administration of DNA Vaccine Influence Immune Responses in Mice and Non-Human Primates. Molecular Medicien 5::287-300.*

A.K. Hall, "Thymosin Beta-10 Accelerates Apoptosis," Cell and Mol. Bio. Res., 1995, 41(3): 167-180.

V.T. Nachmias, "Small Actin-Binding Proteins: the β-Thymosin Family," Current Opinion in Cell Biology, 1993, 5: 56-62.

E. Vasile et al., "Differential Expression of Thymosin β-10 by Early Passage and Senescent Vascular Endothelium is Modulated by VPF/VEGF: Evidence for Senescent Endothelial Cells In Vivo at Sites of Atherosclerosis," The FASEB Jnl., 2001, 15: 458-466.

* cited by examiner

SEQUENCE LISTING

```
<160> NUMBER OF SEQ ID NOS: 14

<210> SEQ ID NO 1
<211> LENGTH: 18
<212> TYPE: DNA
<213> ORGANISM: Artificial Sequence
<220> FEATURE:
<223> OTHER INFORMATION: Tbeta up primer

<400> SEQUENCE: 1
cgggctcgga acgagagt                                                 18

<210> SEQ ID NO 2
<211> LENGTH: 24
<212> TYPE: DNA
<213> ORGANISM: Artificial Sequence
<220> FEATURE:
<223> OTHER INFORMATION: Tbeta down primer

<400> SEQUENCE: 2
cgcctcactt taaaggattc tagg                                          24

<210> SEQ ID NO 3
<211> LENGTH: 24
<212> TYPE: DNA
<213> ORGANISM: Artificial Sequence
<220> FEATURE:
<223> OTHER INFORMATION: thymosin up primer

<400> SEQUENCE: 3
tcggaacgag actgcacgga ttgt                                          24

<210> SEQ ID NO 4
<211> LENGTH: 24
<212> TYPE: DNA
<213> ORGANISM: Artificial Sequence
<220> FEATURE:
<223> OTHER INFORMATION: thymosin down primer

<400> SEQUENCE: 4
gttagcctga cggtttaaga ggcc                                          24

<210> SEQ ID NO 5
<211> LENGTH: 28
<212> TYPE: DNA
<213> ORGANISM: Artificial Sequence
<220> FEATURE:
<223> OTHER INFORMATION: S9 up primer

<400> SEQUENCE: 5
gatgagaagg acccacggcg tctgttcg                                      28

<210> SEQ ID NO 6
<211> LENGTH: 28
<212> TYPE: DNA
```

```
<213> ORGANISM: Artificial Sequence
<220> FEATURE:
<223> OTHER INFORMATION: S9 down primer

<400> SEQUENCE: 6
acagggagga cccgacgacc taacagag                                            28

<210> SEQ ID NO 7
<211> LENGTH: 18
<212> TYPE: DNA
<213> ORGANISM: Artificial Sequence
<220> FEATURE:
<223> OTHER INFORMATION: thymosin full up primer

<400> SEQUENCE: 7
cgggctcgga acgagact                                                      18

<210> SEQ ID NO 8
<211> LENGTH: 18
<212> TYPE: DNA
<213> ORGANISM: Artificial Sequence
<220> FEATURE:
<223> OTHER INFORMATION: thymosin full down primer

<400> SEQUENCE: 8
ggttagcctg acggttta                                                      18

<210> SEQ ID NO 9
<211> LENGTH: 20
<212> TYPE: DNA
<213> ORGANISM: Artificial Sequence
<220> FEATURE:
<223> OTHER INFORMATION: E1A up primer

<400> SEQUENCE: 9
agctgatcga agaggtactg                                                    20

<210> SEQ ID NO 10
<211> LENGTH: 19
<212> TYPE: DNA
<213> ORGANISM: Artificial Sequence
<220> FEATURE:
<223> OTHER INFORMATION: E1A down primer

<400> SEQUENCE: 10
gagtcacagc tatccgtac                                                     19

<210> SEQ ID NO 11
<211> LENGTH: 22
<212> TYPE: DNA
<213> ORGANISM: Artificial Sequence
<220> FEATURE:
<223> OTHER INFORMATION: E1B up primer

<400> SEQUENCE: 11
ggttacatct gacctcatgg ag                                                 22

<210> SEQ ID NO 12
<211> LENGTH: 22
<212> TYPE: DNA
<213> ORGANISM: Artificial Sequence
<220> FEATURE:
<223> OTHER INFORMATION: E1B down primer

<400> SEQUENCE: 12
cagtacctca atctgtatct tc                                                 22
```

-continued

```
<210> SEQ ID NO 13
<211> LENGTH: 20
<212> TYPE: DNA
<213> ORGANISM: Artificial Sequence
<220> FEATURE:
<223> OTHER INFORMATION: control up primer

<400> SEQUENCE: 13
tcgtttctca gcagctgttg                                               20

<210> SEQ ID NO 14
<211> LENGTH: 20
<212> TYPE: DNA
<213> ORGANISM: Artificial Sequence
<220> FEATURE:
<223> OTHER INFORMATION: control down primer

<400> SEQUENCE: 14
catctgaact caaagcgtgg                                               20
```

METHOD FOR USING THYMOSIN β-10 FOR GENE THERAPY OF SOLID MALIGNANT TUMORS

CROSS-REFERENCE TO RELATED APPLICATION

This application claims the benefit of priority to Korean Patent Application No. 2001-63524, filed Oct. 10, 2001, the entire contents of which are incorporated herein by reference.

FIELD OF THE INVENTION

The present invention relates to a method for using thymosin β-10 for cancer treatment by expressing thymosin β-10 in solid malignant tumor cells. More precisely, the present invention relates to a cancer treatment method wherein thymosin β-10 is expressed in solid malignant tumor cells by infecting adenovirus including thymosin β-10. The gene therapy for cancer using thymosin β-10 of the present invention is very effective for the treatment of ovarian cancer, cervical cancer, stomach cancer and lung cancer.

BACKGROUND OF THE INVENTION

Gene therapy is a kind of treatment for genetic diseases and cancers caused by aberration of genes, whose mechanism is to introduce disease-related genes directly to patients in order to normalize the cell function by expressing those genes inside cells. Gene therapy is very effective not only for the treatment of diseases, but also for prevention of many diseases and even more reinforcing the treatment since the therapy can bestow new function on human body by introducing a specific gene.

The crucial point of gene therapy is how introduced genes can be transferred to the nuclei of target cells successfully for mass expression of the genes. After reaching target cells, the introduced genes enter the cells through endocytosis and are expressed in nuclei of the cells. DNA genes can be introduced with liposome, a kind of carrier, because DNA itself cannot pass through cell membrane well. In that case, however, most of the liposome might be destroyed in the middle of transferring into nuclei of the cells, resulting in low transferring efficacy.

Using virus for gene therapy is desirable since foreign genes can be inserted into cells effectively with infectious virus. Particularly, curable genes ought to be inserted in virus DNA by the genetic recombination method and then a great amount of those foreign gene inserted in virus are produced in vitro. By infecting human body with the virus, the curable genes can be transferred into human cells and expressed effectively. Especially, adenovirus can transfer its gene into nuclei of cells, which makes it useful for gene therapy with such effective transmission.

Thymosin β-4, β-10 and β-15 act as major actin monomer-sequestering factors. Thymosin β-4 has 43 amino acids and shares a high degree of homology(85%) at the amino acid level with thymosin β-10. A number of investigations have now suggested that the role of thymosin β-4 and β-10 may be related to mechanisms associated with cell division and/or differentiation. Despite these gene's structural and functional similarities, different expression patterns have been observed. For example, while both thymosins were strongly expressed in fetal brain and other fetal organs, thymosin β-10 levels fell considerably in most adult tissues, and thymosin β-4 expression was down-regulated in metastatic cells of colorectal carcinomas(Hall et al., *Mol. Brain Res.*, 1990, 8:129–135; Hall et al., *Mol. Cell. Endocrinol.*, 1991, 79:37–41; Yamamoto et al., *Biochem. Biophys. Res. Commun.*, 1993, 193:706–710). Another recently discovered member of the β-thymosin family, thymosin β-15, is upregulated in aggressive human prostate cancer (Bao et al., *Nat. Med.*, 1996, 2:1322–28). It is expressed in highly motile, metastatic prostate cancer cells as well as in advanced human prostate and breast cancer (Eadie et al., *J. Cell, Biochem.*, 2000, 77:277–287; Gold et al., *Mod. Pathol.*, 1997, 10:1106–12). Thymosin β-15 differs from other β-thymosins in that its expression correlates with motility and metastasis in highly metastatic prostate carcinoma cells.

Thymosin β-10 is a small actin-binding protein known to sequester actin monomers and thereby induce depolymerization of the intracellular F-actin networks (Nachmias, *Curr. Opin. Cell Biol.*, 1993, 5:56–62; Yu et al., *J. Biol. Chem.*, 1993, 268:502–9; Yu et al., *Cell Motil. Cytoskeleton*, 1994, 27:13–25). Actin is one of the most abundant structural proteins in the cell (Pollard and Cooper, *Ann. Rev. Biochem.*, 1986, 55:987–1035), and the dynamic equilibrium between monomeric and filamentous actin is shown to be altered in neoplastic/transformed cells (Hall, *Ren Fail.*, 1994, 16:243–54). Alteration of thymosin β-10 expression may thus affect the cellular infrastructure by changing the actin stress fiber, which may further alter the balance of cell growth, cell death, cell attachment and cell migration (Yu et al., *J. Biol. Chem.*, 1993, 268:502–9). During embryogenesis, thymosin β-10 is also highly expressed (Carpintero et al., *FEBS Lett.*, 1996, 394:103–6), which is consistent with constant cell migration and morphogenesis that require cell detachment. Thymosin β-10 was also shown to be involved in inducing processes leading to cell detachment (Iguchi et al., *Eur. J. Biochem.*, 1998, 253:766–770). Thymosin β-10 has also been proposed to have dual functions: programmed cell death and invasion or metastasis (Hall, *Cell. Mol. Biol. Res.*, 1995, 41:167–180; Marian et al., *Int. J. Cancer*, 1993, 53:278–84).

Differentially expressed genes in normal and cancer cells have recently been identified in order to find novel tumor markers and understand the pathways of cancer development and progression. cDNA microarray is an effective high-throughput method of examining large-scale differential gene expression patterns of specific cDNA populations on a single blot (DeRisi et al., *Nat. Genet.*, 1996, 14:457–60). Fuller et al. successfully used this approach to determine that insulin-like growth factor binding protein 2(IGFBP2) is overexpressed in glioblastoma multiforme (Fuller et al., *Cancer Res.*, 1999, 59:4228–32), and Huang et al. identified superoxide dismutase as a target for the selective killing of cancer cells (Huang et al., *Nature*, 2000, 407:390–95). An alternative method of gene-expression profiling is the serial analysis of gene expression (SAGE) (Velculescu et al., *Science*, 1995, 170:484–7; Zhang et al., *Science*, 1997, 276:1268–72; Hough et al., *Cancer Res.*, 2000, 60:6281–7). An effort to profile gene expression using SAGE was launched by NCBI, and a public database is available for increasing numbers of normal and neoplastic human cell lines and tissues (http://www.sagenetnet.org).

In order to identify proper genes useful for gene therapy for solid malignant tumors, the present inventors searched abnormally expressed genes in solid malignant tumor cells, comparing to normal cell tissues and at last discovered that the expression of thymosin β-10 is decreased remarkably in ovarian cancer cell tissues, compared to normal ovarian cells. And finally, the present inventors have accomplished the present invention by discovering that thymosin β-10 could be used for gene therapy for ovarian cancer, cervical cancer and lung cancer, since thymosin β-10 expressed in adenovirus could suppress the solid malignant tumor cell growth or induce apoptosis of tumor cells.

SUMMARY OF THE INVENTION

It is an object of this invention to provide a method for using thymosin β-10 for cancer treatment by expressing thymosin β-10 in solid malignant tumor cells.

To accomplish the object, the present invention provides a method for using thymosin β-10 for cancer treatment by expressing thymosin β-10 in solid malignant tumor cells. The method comprises introducing an exogenous thymosin β-10 gene into solid malignant tumor cells to obtain expression of thymosin β-10 in the tumor cells.

The present invention also provides an adenovirus expression vector containing thymosin β-10 gene.

The present invention also provides an adenovirus without replication competent recombinant virus (RCV) by using the above expression vector.

The present invention also provides a method for using the above adenovirus for the treatment of solid malignant tumors. The invention additionally provides a method for inducing apoptosis, inhibiting growth of cancer cells, and/or disrupting F-actin stress fibers in thymosin β-10-deficient cancer cells. The method comprises contacting the thymosin β-10-deficient cancer cells with an expression vector containing an exogenous thymosin β-10 gene.

In a preferred embodiment, the contacting comprises infecting the cancer cells with an adenovirus modified to produce thymosin β-10. The infecting can be by natural viral entry into the cells or by transfection, as is understood by those skilled in the art.

BRIEF DESCRIPTION OF THE DRAWINGS

The application of the preferred embodiments of the present invention is best understood with reference to the accompanying drawings, wherein.

DETAILED DESCRIPTION OF PREFERRED EMBODIMENTS

In one aspect, the present invention provides a method for using thymosin β-10 for cancer treatment by expressing thymosin β-10 in solid malignant tumor cells.

In the preferred embodiments, thymosin β-10 was overexpressed in solid malignant tumor cells to suppress tumor cell growth, induce apoptosis and kill the tumor cells.

Figure 2:
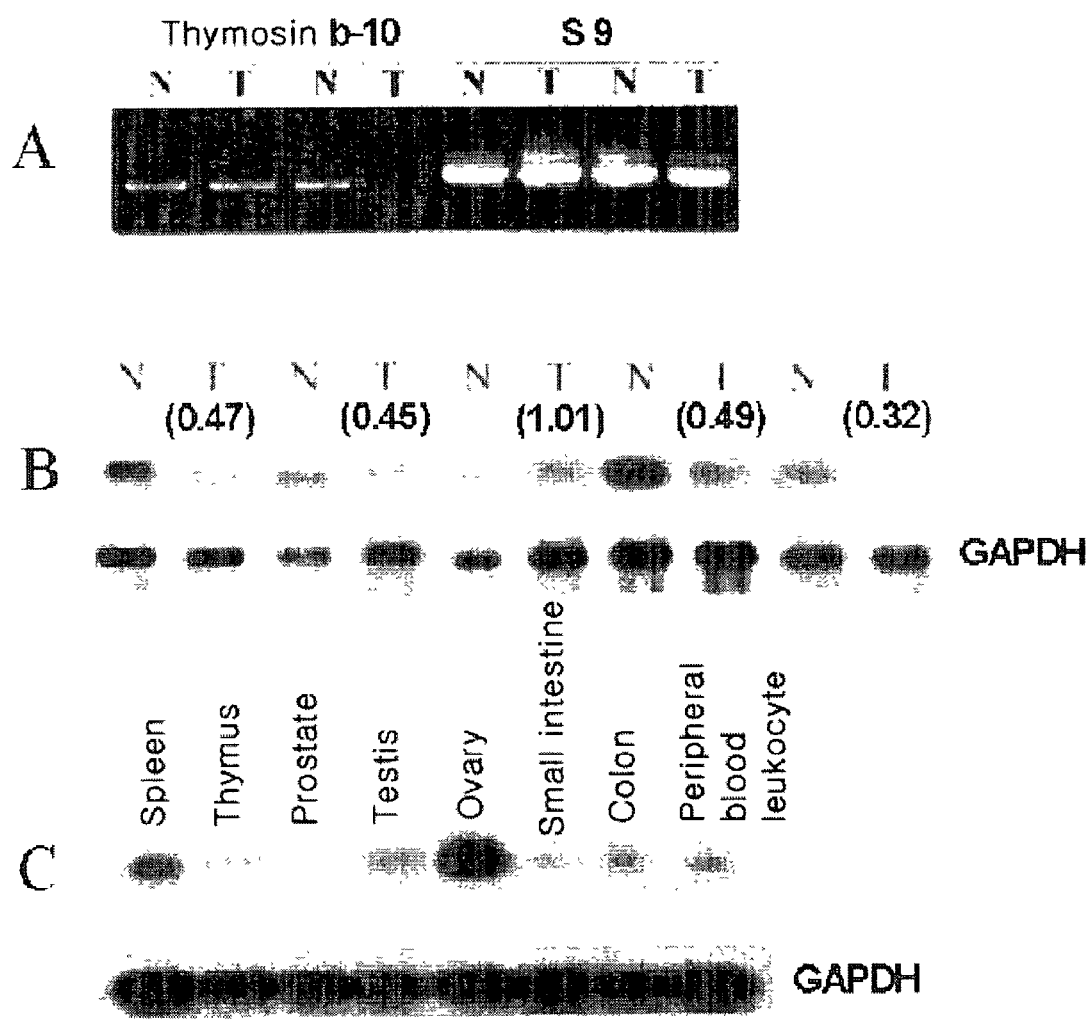
FIG. 2A is a photograph showing the result of Northern blot analysis of thymosin β-10 expression;
N: Normal ovarian,
T: Ovarian cancer tissues
FIG. 2B is a photograph showing the result of PCR analysis of thymosin β-10 expression;
N: Normal ovarian,
T: Ovarian cancer tissues
FIG. 2C is a photograph showing the result of PCR analysis of thymosin β-10 expression (Human ribosomal protein S9 was used as control);
N: Normal ovarian,
T: Ovarian cancer tissues

Thymosin β-10 is expressed at much higher levels in ovarian tissue than in pancreatic, thymus, prostate, testicular and colon tissues. And the expression is decreased in ovarian cancer tissue compared with normal ovarian tissue (see FIG. 2). Thymosin β-10 is a small actin-binding protein known to sequester actin monomers and thereby induce depolymerization of the intracellular F-actin network. Thus, alteration of thymosin β-10 expression may affect the cellular infrastructure by changing the actin stress fiber, which may further alter the balance of cell growth, cell death, etc.

In the preferred embodiments of the present invention, thymosin β-10 whose expression was specifically decreased in solid malignant tumor tissues was expressed in solid malignant tumor cells. Thymosin β-10 expressed in solid malignant tumor cells causes the alteration of actin stress fibers, leading to the suppress of solid malignant tumor cell growth or even to the death of those cancer cells.

In the preferred embodiments of the present invention, thymosin β-10 was used for cancer treatment by expressing thymosin β-10 in solid malignant tumors such as ovarian cancer, cervical cancer, stomach cancer, lung cancer and liver cancer cells.

The present invention also provides a adenovirus expression vector containing thymosin β-10 gene.

The present invention provides a adenovirus expression vector which can produce thymosin β-10 protein by using expression cassette consisting of coding regions for promoter site and multiple cloning site of cytomegalovirus (CMV), late polyadenylation signal site of simian virus 40 (SV 40) and green fluorescence protein (GFP).

In the preferred embodiment of the present invention, it is easy to confirm with GFP if the above expression vector can penetrate into cells since GFP emits green fluorescent light in cancer cells when those cells are infected with adenovirus expression vector.

In the present invention, pQBI-Ad5CMV-GFP vector containing expression cassette consisting of coding regions for promoter site and multiple cloning site of cytomegalovirus (CMV), late polyadenylation signal site of simian virus 40 (SV 40) and green fluorescence protein (GFP) was used. In order to separate thymosin β-10 gene, RT-PCR was performed with primers represented by the SEQ. ID. NO: 1 and 2. At this time, RNA purified from normal tissues was used as a template. Finally, normal human thymosin β-10 cDNA was obtained. The above thymosin β-10 cDNA was inserted into multiple cloning site of pQBI-Ad5CMV-GFP vector, and then Ad-GFP-thymosin β-10 was constructed. The above adenovirus expression vector "Ad-GFP-thymosin β-10" was deposited at Gene Bank of Korea Research Institute for Bioscience and Biotechnology on Oct. 8, 2001 (Accession No: KCTC 10089BP).

The present invention also provides an adenovirus without replication competent recombinant virus (RCV) by using the above expression vector.

As a DNA virus, adenovirus contains E1A gene site essential for virus proliferation in genome and other genes necessary for virus packaging. In order to use adenovirus for gene therapy, genes related to virus proliferation are required to be removed not to cause another disease by self-proliferation and infection in vivo. Thus, eliminating E1A gene site of adenovirus genome which is related to virus proliferation results in safe use of adenovirus for gene therapy because virus can not proliferate itself in normal cells without E1A gene site. In order to prepare adenovirus massively by using the above adenovirus expression vector, sell line for adenovirus packaging was transfected with the above expression vector. 293 cells were used for packaging cell line. 293 cells contain E1A gene site of adenovirus in their chromosome DNA, so that E1A gene is expressed continuously within cells and cells are provided with E1A proteins.

The present invention provides a adenovirus clone without RCV selected from adenovirus proliferation by injecting adenovirus expression vector Ad-GFP-thymosin β-10 into packaging cell line 293 along with adenovirus mother vector.

The present invention also provides a method for using the above expression vector for the treatment of solid malignant tumors.

In the preferred embodiment of the present invention, the present inventors have infected ovarian cancer cells with Ad-GFP-thymosin β-10 in order to detect its effect on ovarian cancer cell growth. As a result, Ad-GFP-thymosin β-10 infected cells showed decreased cell-growth comparing to uninfected or normal cells (see FIG. 5).

The present inventors have infected ovarian cancer cells with Ad-GFP-thymosin β-10 in order to investigate its effect on apoptosis of ovarian cancer cells. As a result, apoptosis of Ad-GFP-thymosin β-10 infected cells was rapidly increased (see FIG. 6), and F-actin stress fibers of infected cells were disrupted because of overexpression of thymosin β-10 (see FIG. 7). As explained above, thymosin β-10 expressed in solid malignant tumor cells cause the alteration of actin stress fibers, leading to the suppress of solid malignant tumor cell growth or even to the death of those cancer cells.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Gene Expression Profiles in Normal Ovary and Ovarian Cancer Tissues

In order to analyze gene expression in tissues of normal and neoplastic ovaries, the present inventors used the cDNA expression array. Putative candidate genes were confirmed by polymerase chain reaction (PCR) and Northern blot analysis and selected for further characterization.

<1-1> Tissues and RNA Isolation

Ovarian cancer tissues were obtained from patients of the Department of Obstetrics and Gynecology, Samsung Medical Center, Seoul, Korea. The disease stage of the tissue sample was assigned according to the classification proposed by the clinical staging criteria of the International Federation of Gynecology and Obstetrics (FIGO). Five pairs of normal and ovarian cancer tissues-one papillary serous adenocarcinoma (stage IIIc), one borderline mucinous ovarian tumor (stage Ic), one serous cystadenocarcinoma (stage IIIc) and two clear-cell carcinomas (stage Ic)-were used. The tissues were frozen in liquid nitrogen and stored at −70° C.

Before RNA extraction, a part of each tissue sample was sliced by paraffin section and examined by hematoxylin and eosin staining. Tissue samples containing more than 50% tumor cells were used in the present invention. We, the present inventors, obtained paired normal tissues from uninvolved ovaries for each individual patient, followed by microscopically examining them to confirm that the tissue contained no malignant cells.

Total RNAs were obtained by extracting tissues in Trizol (Life Technologies, Gaithersburg, Md., USA) according to the manufacturer's instructions. Normal ovarian tissues and ovarian cancer tissues (about 100 mg of each) were homogenized in Trizol solution (1 Ml) using a Polytron homogenizer (Brinkman, Switzerland). Homogenates were incubated for 10 minutes on ice, and 0.2 volume of chloroform was added to the homogenates. After vigorous agitation for 5 minutes, the inorganic phase was separated by centrifugation at 12,000 g for 20 minutes at 4° C. RNAs were then precipitated in the presence of one volume of isopropanol. RNA pellets were washed with 70% ice-cold ethanol, and then dissolved in RNase-free water. Total RNA concentration was assessed by absorbency at 260 nm using an ultraviolet spectrophotometer (Biochrom LKB, UK).

<1-2> $^{32}$P-Labeled cDNA Synthesis $^{32}$P-labeled cDNAs were synthesized with the use of total RNA from both normal and tumor tissues isolated in the above <1-1> by reverse transcription in the presence of [$^{32}$P]dCTP. Particularly, total RNAs (20 μg each) were denatured at 75° C. for 10 minutes in the presence of 8 pmol of dT$_{15}$VN (V=A, G and C; N=A, G, C and T) mixture. After the denaturation step, cDNAs were synthesized by incubation at 37° C. for 1 hour in a master mix (total reaction volume, 40 μl) containing 3 μl of dNTP (500 μM, without dCTP), 5 μl [$^{32}$P]dCTP (3000 Ci/mmol; Amersham Life Science, Cleveland, Ohio, USA) and 1,600 Units of MMLV reverse transcriptase (Promega, Madison, Wis., USA) in 1×RT buffer (Promega). The reaction was terminated by heating for 10 minutes at 75° C., and unincorporated nucleotides were removed by gel purification (Chroma spin-200; Clontech). For each reaction, about 2×10⁷ c.p.m. was incorporated in the final product.

<1-3> cDNA Microarray Hybridization

³²P-labeled cDNAs synthesized in the above <1-2> were denatured by boiling for 5 minutes and then hybridized to Atlas 1 human cDNA array blots (Clontech; http://www.clontech.com/atlas/gene-lists/Hbroad.txt) in hybridization solution (ExpressHyb hybridization solution, Clontech). Membranes were prehybridized at 68° C. at least for 2 hours before probe addition. Hybridization was performed at 68° C. in a rolling bottle overnight. After the first two washes with 2×SSC (1×SSC; 0.15 M NaCl, 15 mM sodium citrate, pH 7.0) and 0.1% SDS at 68° C. for 20 minutes, the membranes were subjected to a stringent wash with 0.1× SSC, 0.5% SDS and 0.1 mM EDTA at 68° C. Membranes were then exposed to X-ray film (Hyperfilm, Amersham) for 1 or 3 days at −70° C. To normalize the relative gene expression, the present inventors selected the GADPH and ribosomal protein S9 gene as internal references.

Figure 1:
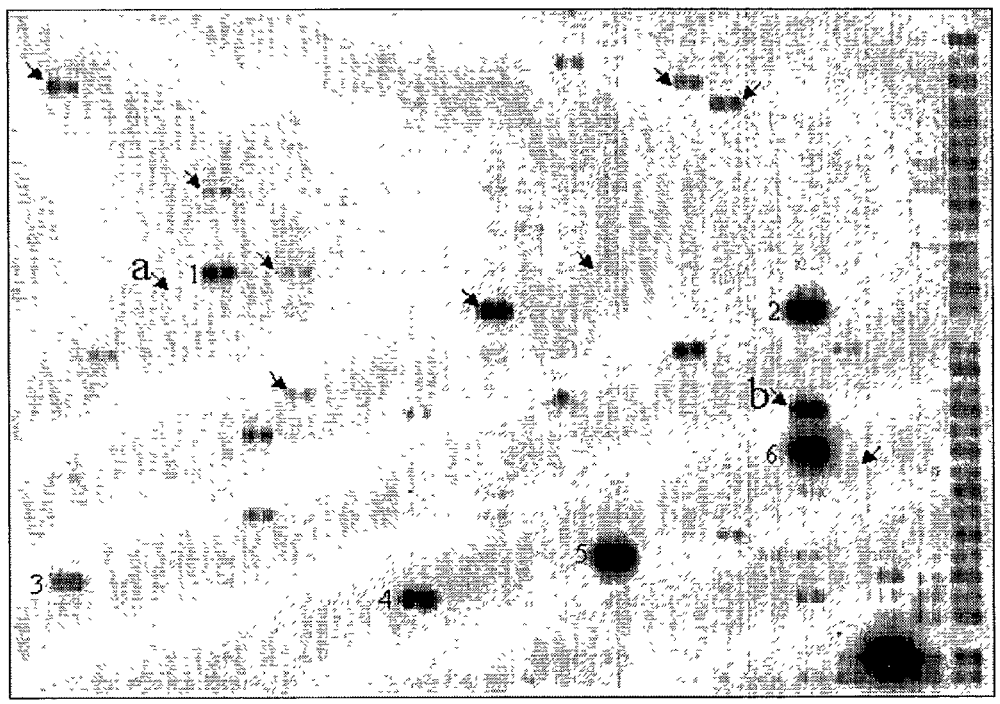
FIG. 1 is photographs showing the results of parallel analysis of gene expression in human normal ovary and ovarian cancer using the cDNA expression array;
A: Normal ovary, B: Ovarian cancer tissue,
→: cDNA spots that show significant differences in gene expression,
a: Smad 1, b: Thymosin β-10
1–6: Constitutively expressed genes in human ovary,
1: RPS19, 2: Mch4, 3: RPL6, 4: Interleukin-2 receptor α, 5: Integrin αL, 6: TDGF3
Figure 1:
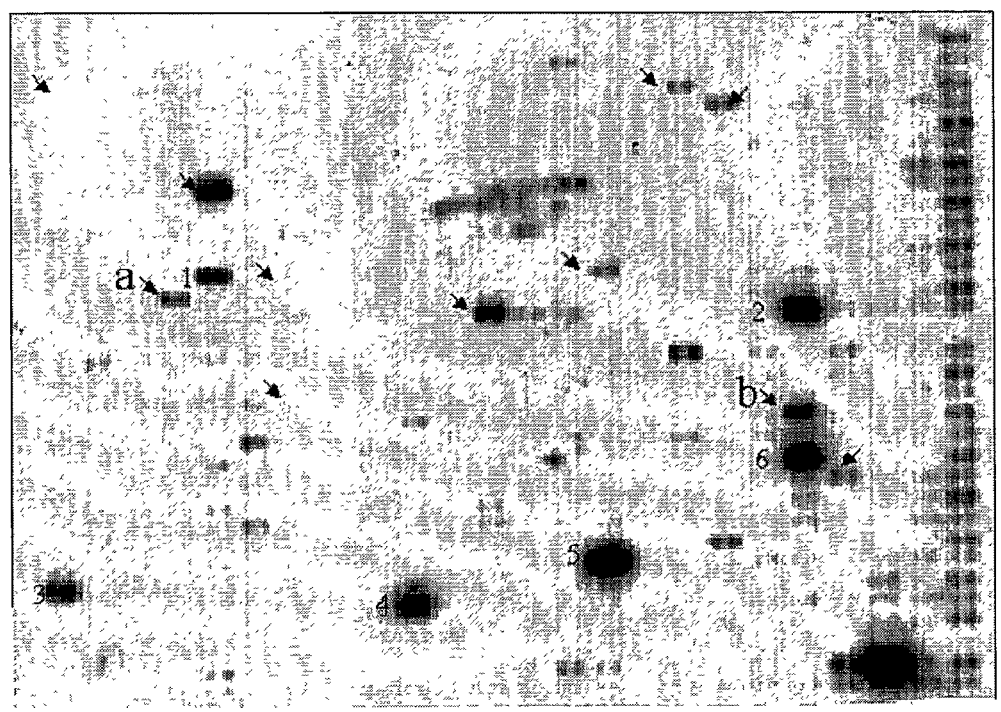

As a result, the expression profiles of 588 genes in normal ovarian and ovarian tumor tissues were obtained. Results from one pair of sample are shown in FIG. 1. By comparing hybridized blots of normal and tumor tissues, the present inventors identified several genes whose expressions were changed. As marked by arrows in FIG. 1, no signal was visible in blank spots and negative control spots (M13 DNA, λphage DNA and pUC18 DNA), indicating that the hybridization was highly specific.

Expression levels of specific genes, either increased or decreased, were quantified by densitometric scanning of hybridized signals. The quantification results are summarized in Tables 1 and 2. Only genes with expression levels that were altered more than two fold in comparisons of normal and cancer samples, and in more than two of the ovarian cancer samples, are included. Gene expression was normalized up to the level of that of housekeeping gene GADPH. Similar expression patterns for these genes were obtained in independent cDNA array hybridization experiments.

TABLE 1

| Position | Name of protein/Gene | Case 1 | Case 2 | Case 3 | Case 4 | Case 5 |
|---|---|---|---|---|---|---|
| A4m | Mothers against DPP protein (Smad1) | + | + | + | + | NC |
| A5h | Prothymosin alpha | + | NC | + | + | NC |
| A7e | TOB(+) | NC | + | + | + | NC |
| A71 | C-1 | + | NC | NC | + | + |
| B71 | Heat shock (heat shock 27 kDa protein 1) | + | NC | NC | + | + |
| F5g | Insulin-like growth factor IA | + | NC | NC | NC | + |

+: Expression increased,
NC: Not changed,
Case 1: Papillary serous adenocarcinoma (stage IIIc),
Case 2: Borderline mucinous ovarian tumor (stage Ic),
Case 3: Serous cystadenocarcinoma (stage IIIc),
Case 4, 5: Clear-cell carcinomas (stage Ic).

TABLE 2

| Position | Name of protein/Gene | Case 1 | Case 2 | Case 3 | Case 4 | Case 5 |
|---|---|---|---|---|---|---|
| A1c | MYB proto-oncogene protein | − | − | NC | NC | NC |
| B4n | Tyrosine-protein kinase JAK1 | − | − | NC | NC | NC |
| C1c | Tumor necrosis factor receptor | − | NC | NC | − | NC |
| C2d | Tyrosine kinase ligand | − | − | − | NC | NC |
| C5e | HDLC1 (cytoplasmic dynein light chain 1) | NC | − | − | NC | NC |
| D1d | DNA binding protein inhibitor ID-3 | NC | − | − | NC | − |
| D1g | DNA binding protein inhibitor ID-2 | NC | NC | − | − | − |
| D3k | Guanine nucleotide-binding protein G-S (alpha subunit) | NC | − | NC | − | − |
| D5h | DNA binding protein SATB1 | NC | − | − | − | NC |
| D5k | Transcription factor PAX3/FORKHEAD | NC | NC | − | − | − |
| D7c | Proliferation-associated protein PAG | − | − | NC | − | NC |
| F4d | Thymosin beta-10 | − | − | − | NC | - |

−: Expression decreased,
NC: Not changed,
Case 1: Papillary serous adenocarcinoma (stage IIIc),
Case 2: Borderline mucinous ovarian tumor (stage Ic),
Case 3: Serous cystadenocarcinoma (stage IIIc),
Case 4, 5: Clear-cell carcinomas (stage Ic).

As shown in Tables 1 and 2, six genes showed increased expression in ovarian cancer tissues: Smad1 (Mothers against DPP protein), prothymosin alpha, Tob, C-1, heat shock 27-kDa protein 1, and insulin-like growth factor (Table 1). The expression of 12 genes was decreased in ovarian cancer tissues, including a group of apoptosis-related proteins, DNA-binding proteins, DNA-binding protein inhibitors, transcription factors and thymosin β-10 (Table 2). Among them, thymosin β-10 showed consistently decreased expression levels in four of five cancer samples.

Example 2

Analysis of Thymosin β-10 Expression Pattern

In order to investigate the expression pattern of thymosin β-10 showing decreased expression levels in ovarian cancer tissues, the present inventors performed Northern blot and PCR.

<2-1> Northern Blot

For Northern blot hybridization, total RNA extracted from five pairs of normal and ovarian cancer tissues in the above example <1-1> was used. Total RNA(10 μg) was denatured in the presence of 50% formamide, 2.2 M formaldehyde, 20 mM MOPS(3-[N-morpholino] propanesulfonic acid), 4 mM sodium acetate and 0.5 mM EDTA at 65° C. for 10 minutes. After electrophoresis in a 1.2% agarose gel containing 2.2 M formaldehyde, RNA was transferred onto a nylon membrane (Nytran, 0.45-μm pore size; Schleicher and Schuell, Germany) by capillary action under 10×SSPE (1×SSPE; 0.18 M NaCl, 10 mM Na₂HPO₄ [pH 7.7], 1 mM EDTA). RNA transfer and loading efficiency was estimated by staining a separate membrane with 0.1% methylene blue. RNA intactness was estimated by comparing the intensities of the 28S and 18S ribosomal RNA bands. For hybridization, the membrane was washed in 6×SSPE for 5 minutes and air-dried, and the RNA was permanently attached to the membrane by 1 minute UV illumination. Hybridization was performed overnight in a heat-sealable polyethylene bag containing 40 Ml of hybridization buffer (5×SSPE[PH 7.4], 5×Denhardt's solution, 0.5% SDS, 0.2 mg/Ml heat-denatured salmon sperm DNA, 50% formamide) and the hybridization probe. The thymosin β-10 cDNA(178 bp) probe containing the entire coding sequence was obtained by PCR amplification with the primers represented by the SEQ. ID. NO: 1 and 2. $^{32}$P-labeled cDNA probes were synthesized using a Rediprime cDNA synthesis kit (Amersham).

As a result, Northern blot analysis confirmed decreased thymosin β-10 mRNA levels in four of five ovarian tumors (FIG. 2A). In FIG. 2A, the numbers below each T lane represent the ratio of hybridization signals in cancer/normal tissues.

<2-2> PCR Analysis

In order to confirm the differential expression of thymosin β-10, the present inventors performed PCR analysis of thymosin β-10 with two matched human ovarian cDNA pairs(tumor versus normal; Clontech Laboratories, Palo Alto, Calif., USA) as templates. The first fair was the cDNA of ovary serous cystadenocarcinoma and normal tissue, and the second fair was the cDNA of ovary papillary serous carcinoma and normal tissue. PCR was performed at the following cycles: 30 seconds at 94° C.; 30 cycles of 30 seconds at 94° C.; 1 minute at 68° C.; 1 minute at 72° C.; 5 minutes at 72° C., according to the manufacturer's protocols (Clontech). The present inventors used primers represented by the SEQ. ID. NO: 3 and 4 for thymosin β-1, and we used human ribosomal protein S9 primers represented by the SEQ. ID. NO: 5 and 6 as control.

As a result, thymosin β-10 expression was decreased in cancer cells in one of the two pairs (FIG. 2B).

<2-3> Thymosin β-10 Expression in Normal Ovary and Other Organs

In order to confirm the expression pattern of thymosin β-10 in various normal tissues, total RNA was isolated from normal spleen, thymus, prostate, testis, ovary, small intestine, colon and peripheral blood leukocytes, and Northern blot analysis was performed with the total RNA by the same method as in Example <2-1>.

As a result, thymosin β-10 expression was found to be highest in normal ovary compared with other organs examined, including spleen, thymus, prostate, testis, small intestine, colon and peripheral blood leukocytes(FIG. 2C). From the above results, it was suggested that thymosin β-10 is downregulated in human ovarian cancer and may play an important role in human ovarian carcinogenesis.

Example 3

Analysis of Thymosin β-10 Expression Pattern by SAGE

In order to confirm the expression pattern of thymosin β-10 in ovarian cancer versus normal cells, the present inventors analyzed the data of its expression in the ovarian SAGE(serial analysis of gene expression) libraries available at the NCBI database (Hough, et al., Cancer Res., 2000, 60:6281–87).

For SAGE analysis, the frequencies of tags represent the relative expression of the genes in the cell population. As shown in Table 3, similar frequencies for thymosin β-10 were seen in a normal ovarian epithelial cell line, an SV40 large T antigen-transformed ovarian epithelial cell line, and three of ten tumors, whereas lower frequencies were found in six of the 10 tumors; the frequency of thymosin β-10 expression was increased only in one case of them.

From the above results, it was suggested that thymosin β-10 is downregulated in approximately 60% of ovarian cancers and may play an important role in the development of this subset of ovarian cancers.

TABLE 3

| Pathology | | Name | Frequency | |
|---|---|---|---|---|
| Normal | Surface epithelium | HOSE4 | 106 | high |
|  | Surface epithelium cell line | IOSE29-11 | 91 | high |
| Cancer | Cancer cell line | A2780-9 | 15 | low |
|  | Clear cell carcinoma | ES2-1 | 94 | high |
|  | Cystadenoma line | ML10-10 | 112 | high |
|  | Serous | OC14p | 13 | low |
|  | Carcinoma cell line | OV1063-3 | 22 | low |
|  | Carcinoma cell line | OVCA432-1 | 3 | low |
|  | Pooled cancer lines | OVP-5 | 7 | low |
|  | Serous | OVT-6 | 82 | high |
|  | Serous | OVT-7 | 176 | high |
|  | Serous | OVT-8 | 27 | low |

Example 4

Construction of Adenovirus Expression Vector Containing Thymosin β-10

In order to construct adenovirus expression vector containing thymosin β-10, firstly, thymosin β-10 gene was isolated. Particularly, full-length human thymosin β-10 (349 bp) was amplified by using the primers represented by the SEQ. ID. NO: 7 and 8. The amplified human thymosin β-10 fragment was cloned into pCRII-TOPO vector (Invitrogen).

The cloning product was confirmed for sequence from both directions, and named as "pCR-TOPO-thymosin β-10".

Figure 3:
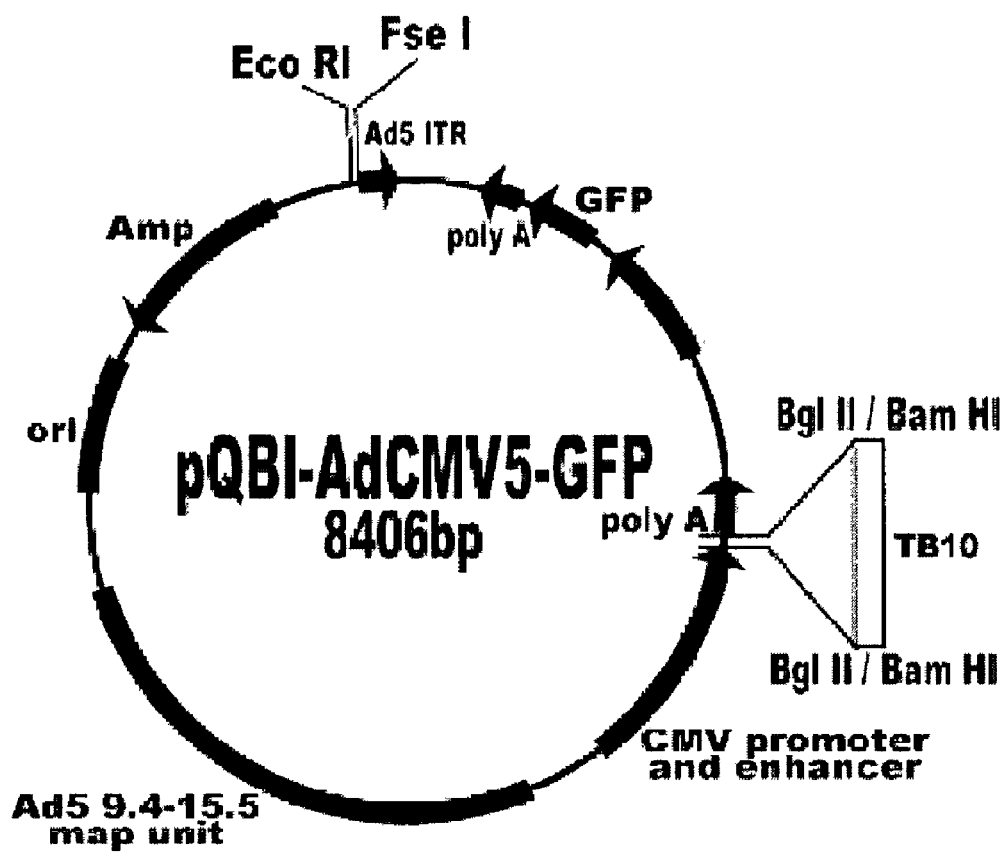
FIG. 3 is a schematic diagram showing the genetic map of adenovirus expression vector containing the thymosin β-10 gene.

The pCR-TOPO-thymosin β-10 was digested with EcoRI and cloned into the pΔACMV EcoRI site. The BamHI fragment of thymosin β-10 was inserted into the BglII site of pQBI-Ad5CMV-GFP vector(Quantum, Canada), and it was named as "Ad-GFP-thymosin β-10" (FIG. 3). pQBI-Ad5CMV-GFP vector having 9.4–15.5 map units has been used as a shuttle vector of adenovirus backbone vector pJM17, and GFP (Green Fluorescence Protein) of the vector makes it easy to analyze gene transmission under the condition of virus infection.

The above-mentioned expression vector "Ad-GFP-thymosin β-10" of the present invention was deposited at Gene Bank of Korea Research Institute of Bioscience and Biotechnology on Oct. 8, 2001 (Accession No.: KCTC 10089BP).

Example 5

Construction of Adenovirus Clone without RCV Which can Produce Thymosin β-10 Proteins within Cells In order to construct adenovirus clone which can produce thymosin β-10 proteins by infecting thereof into cells, the Ad-GFP-thymosin β-10 and a adenovirus mother vector pJM17 (McGrory, et al., Virology, 1988, 163, 614–617) were cotransfected into a packaging cell line, 293 cells by phosphate-calcium method.

The present inventors have confirmed if the separated DNA from the above adenovirus clone has E1A and E1B gene sites of adenovirus type 5 in order to analyze replication competent recombinant virus (RCV) residing in adenovirus prepared by using adenovirus expression vector of the present invention. Particularly, PCR was performed with E1A primers represented by the SEQ. ID. NO: 9 and 10 and E1B primers represented by the SEQ. ID. NO: 11 and 12. At this time, adenovirus was isolated by phenol extraction and ethanol precipitation after treating 0.5% SDS containing 2 mg/Ml of preteinase K. Through the PCR using E1A and E1B primers, E1 gene site existing in RCV was confirmed by 752 and 1818 bp fragments on the agarose gel. When the PCR was performed with E1-unrelated primers represented by the SEQ. ID. NO: 13 and 14, 816 bp fragment was confirmed regardless of the existence of E1 gene.

In order to search the number of RCV and to detect the virus proliferation in cells more sensitively, the present inventors used Zhang's method (Zhang, L., et al., Science, 1997, 276, 1268–1272) with slight modification. Virus was subcultured 3 times in HeLa cells to amplify RCV. Particularly, HeLa cells were infected with virus clone. 48 hours after infection, the cells were lysed by freezing-thawing method. By centrifugation, supernatant of the cell lysate was obtained. Fresh HeLa cells were infected with the supernatant, and cultured. The above process was repeated a couple of times. In order to get virus DNA for PCR, clear cell lysate obtained from subcultured cells was treated with proteinase K, and phenol extraction and ethanol precipitation was performed. The precipitated DNA was resolved in distilled water, and PCR was performed with E1A primers.

Adenovirus clone without RCV was amplified using 293 cells. Cells were lysed and the lysates were centrifuged with CsCl density gradient. Finally, adenovirus clone for gene therapy was prepared by dialysis with PBS containing 10% glycerol and 1 mM $MgCl_2$. The number of plaques of 293 cells was counted to determine titer of adenovirus clone of the present invention.

Example 6

Infection of Ad-GFP-Thymosin β-10 into Human Ovarian Cancer Cells

Two human ovarian cancer cell lines, PA-1 and SKOV3 were infected with adenovirus without RCV prepared in the above Example 5. Efficiency of transfection was assessed using Ad5CMV-GFP, and the rate was over 90% at an M.O.I. (Multipliaty of Infection) of 100 in the PA-1 and SKOV3 cell lines.

The present inventors performed Western blot analysis to confirm whether the thymosin β-10 was expressed in cells infected with the adenovirus. Particularly, cells were lysed and equal amount of cell extracts(10 μg) were electrophoresed on 15% SDS polyacrylamide gel, electrotransferred onto a nitrocellulose membrane, and probed with rabbit anti-thymosin β-10 antibody(provided by Dr Leondiadis L, Institute of Radioisotopes and Radiodiagnostic Products, NCSR Demokritos, Athens, Greece). Thymosin β-10 expression was detected using the enhanced chemiluminescence system (ECL, Amersham).

Figure 4:
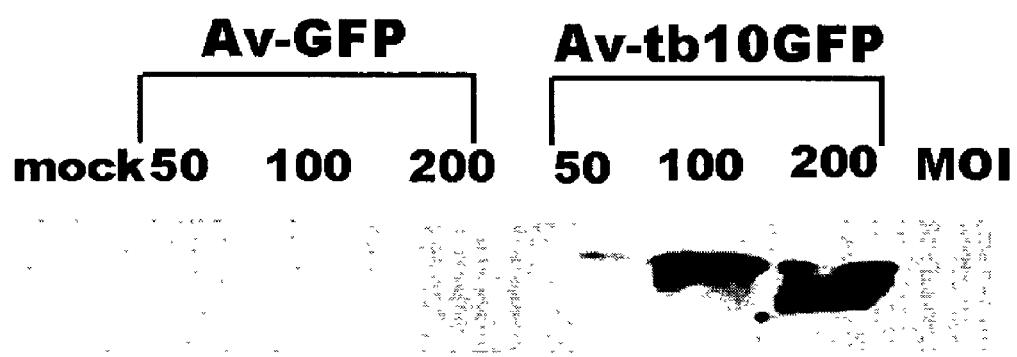
FIG. 4 is a photograph showing the result of Western blot analysis of thymosin β-10 expression in infected PA-1 ovarian cancer cell lines.

As a result, strong expression of thymosin β-10 in the cells infected with adenovirus of the present invention was observed(FIG. 4).

Example 7

Effect of Thymosin β-10 on Ovarian Cancer Cell Growth

The present inventors infected ovarian cancer cell lines with adenovirus prepared in the above Example 5 and observed growth of the cells to investigate the effect of thymosin β-10 on the ovarian cancer cell growth. Particularly, ovarian cancer cells (PA-1 and SKOV3) were plated in triplicate at a density of $2 \times 10^5$ cells/well in 6-well plate. Twenty-four hours later, the cells were infected with Ad-GFP-thymosin β-10. Beginning 24 h after infection, cells were harvested each day, stained with Trypan blue and counted with the light microscope for up to 3 days (PA-1) or up to 5 days (SKOV3).

Figure 5:
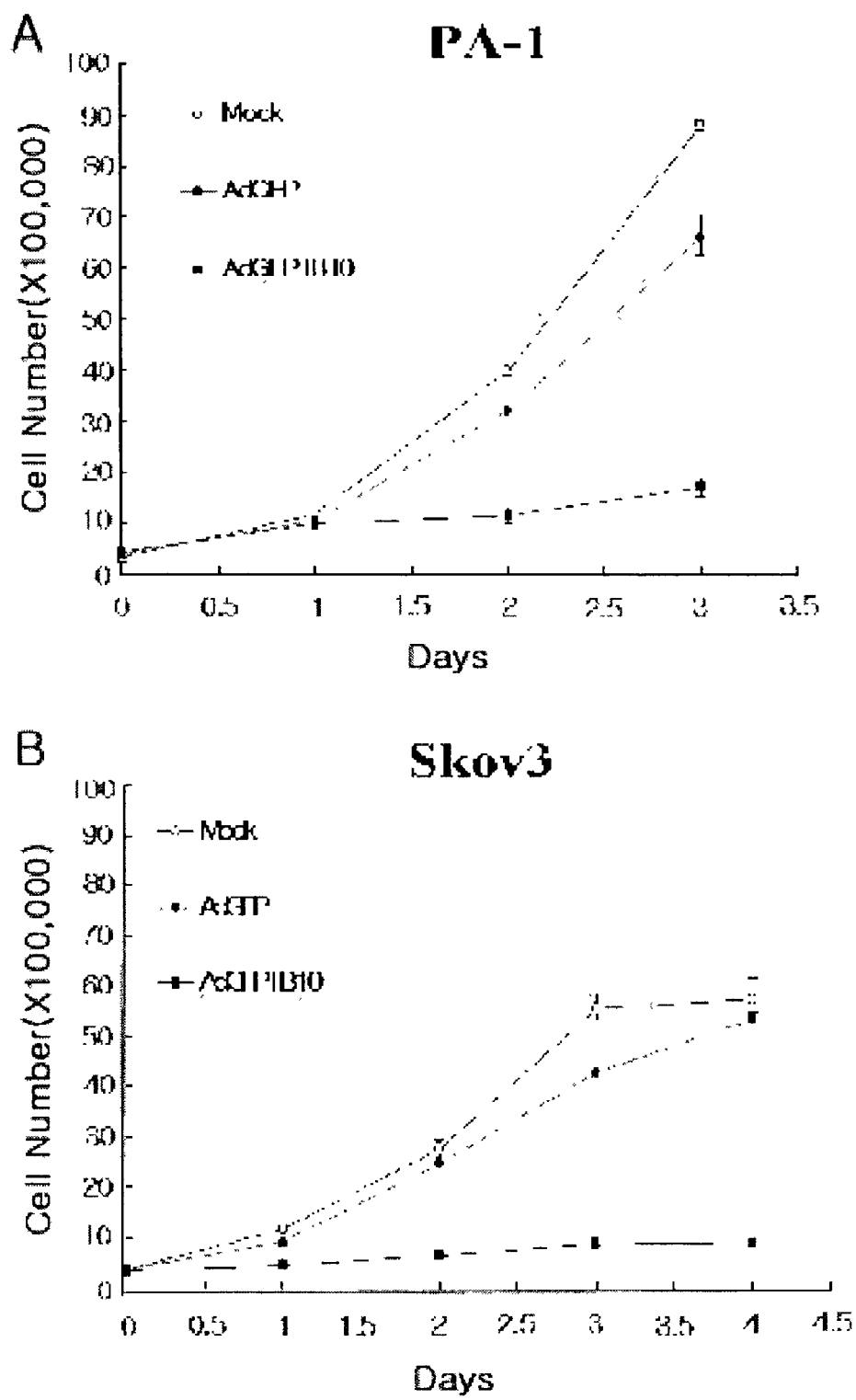
FIG. 5 is graphs showing the effect of thymosin β-10 on the growth of ovarian cancer cell lines PA-1 and SKOV3;
A: PA-1, B: SKOV3,
○: Control, ●: Ad-GFP, ■: Ad-GFP-thymosin β-10

As a result, PA-1 cells infected with adenovirus of the present invention numbered only 20% of mock-infected cells, and SKOV3 cells numbered only 15% of them (FIG. 5).

Example 8

Effect of Thymosin β-10 on Apoptosis of Ovarian Cancer Cells

The present inventors infected ovarian cancer cell lines with adenovirus prepared in the above Example 5 and observed apoptosis of the cells to investigate the effect of thymosin β-10 on the apoptosis of ovarian cancer cells. Particularly, an ovarian cancer cell line, PA-1 cells were plated onto 4-chamber slides (Nalgen Nunc, Inc., Naperville, Ill., USA) at a density of $5 \times 10^4$ cells/well and cultured for 1 day. Two days after infection with Ad-GFP-thymosin β-10 and Ad-GFP, chamber slides were rinsed with phosphate buffered saline(PBS), stained with 2 mg/Ml of DAPI (4,6-diamidino-2-phenylindole, Boehringer Mannheim) at 37° C. for 15 minutes, washed twice with PBS and examined with fluorescence microscope.

Figure 6:
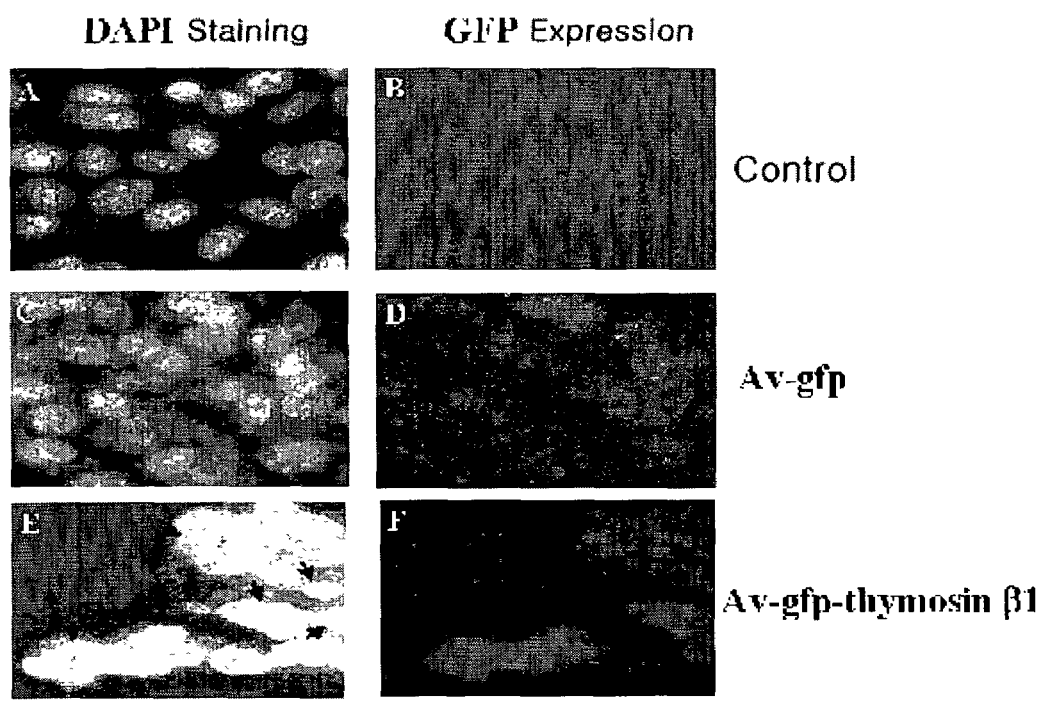
FIG. 6 is microphotographs showing the results analysis of apoptotic cell death induced by Av-GFP or Av-GFP-thymosin β-10 transfection in ovarian cancer cell line PA-1. Cells were stained with DAPI, and GFP expression was examined by fluorescence microscopy;
A,B: Control, C,D: Av-GFP,
E,F: Av-GFP-thymosin β-10

As a result, PA-1 cells infected with adenovirus of the present invention showed clear DNA fragmentation, suggesting that overexpression of thymosin β-10 induced massive cell death (FIG. 6).

Example 9

Effect of Thymosin β-10 on Actin Structure of Ovarian Cancer Cells

Because thymosin β-10 is an actin-binding protein, the present inventors reasoned that thymosin β-10 expression might act by altering actin stress fibers in the cells.

Ovarian cancer cell line PA-1 was infected with adenovirus (Ad-GFP-thymosin β-10) of the present invention, and the cell monolayers were fixed with 4% paraformaldehyde in PBS for 40 minutes at room temperature and then stained with 25 μg/Ml of phalloidin-FITC (Sigma) in the dark for 1 hour. Stained cell monolayers were washed twice with 0.5% triton X-100 in PBS. Coverslips were mounted onto slides using a PBS/glycine mountant and examined with the fluorescence microscope.

Figure 7:
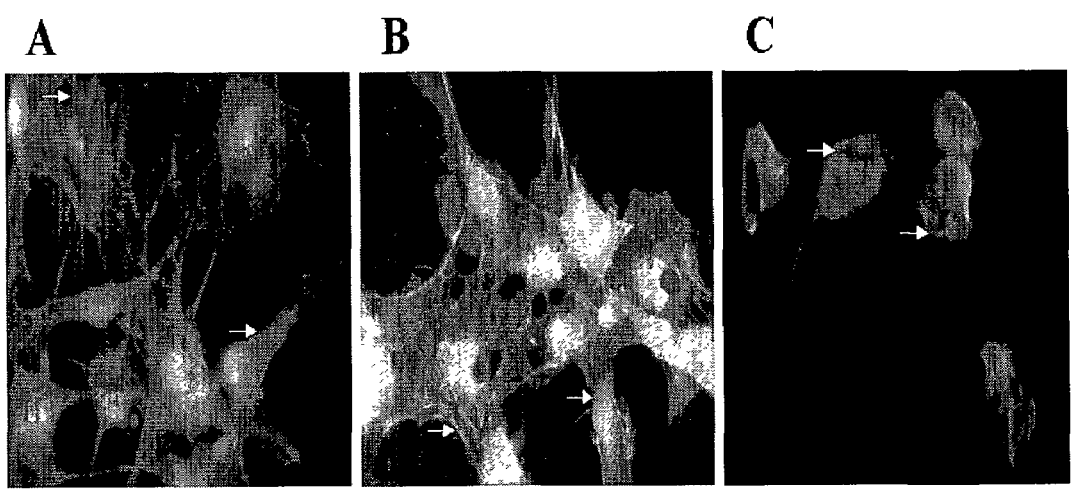
FIG. 7 is microphotographs showing the results of phalloidin-FITC staining assay, which shows structural changes of actin induced by Av-GFP or Av-GFP-thymosin β-10 transfection in ovarian cancer cell line PA-1;
A: Control, B: Av-GFP, C: Av-GFP-thymosin β-10
→: Actin stress fiber

As a result, PA-1 cells infected with mock or Ad-GFP were confirmed to have intact and pervasive actin structure, but the F-actin stress fibers in the cells infected with Ad-GFP-thymosin β-10 were disrupted, suggesting that overexpression of thymosin β-10 induced degradation of F-actin stress fibers (FIG. 7).

As shown above, a cancer treatment method in which thymosin β-10 is expressed in solid malignant tumor cells by infecting adenovirus including thymosin β-10 of the present invention can be effectively used for gene therapy for the treatment of ovarian cancer, cervical cancer, stomach cancer, lung cancer and liver cancer.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

Throughout this application, various references are cited. The entire contents of these references are incorporated herein by reference to describe more fully the state of the art to which the invention pertains.

The invention claimed is:

1. A method for inhibiting the growth of ovarian cancer cells deficient in expression of thymosinβ-10 comprising directly introducing an effective amount of an expression vector containing an exogenous thymosin β-10 gene, operably linked to a promoter, into said ovarian cancer cells under conditions sufficient to permit expression of the exogenous thymosin β-10 gene, thereby inhibiting the growth of ovarian cancer cells.

2. The method according to claim 1, wherein the expression vector is adenovirus expression vector.

3. The method according to claim 2, wherein the adenovirus expression vector is replication incompetent recombinant virus.

4. The method according to claim 2, wherein the adenovirus expression vector is Ad-GFP-thymosin β-10 (Accession Number: KCTC 10089BP).

* * * * *